US006171778B1

(12) United States Patent
Ellington et al.

(10) Patent No.: US 6,171,778 B1
(45) Date of Patent: *Jan. 9, 2001

(54) USE OF ARABINOGALACTAN IN A SPERM WASH PRODUCT

(75) Inventors: Joanna E. Ellington, Valleyford; Sylvia Adams Oliver, Spokane, both of WA (US)

(73) Assignee: Advanced Reproduction Technologies, Inc., Valleyford, WA (US)

( * ) Notice: Under 35 U.S.C. 154(b), the term of this patent shall be extended for 0 days.

This patent is subject to a terminal disclaimer.

(21) Appl. No.: 09/232,269

(22) Filed: Jan. 15, 1999

Related U.S. Application Data

(63) Continuation of application No. 08/599,595, filed on Feb. 9, 1996, now Pat. No. 5,879,877.

(51) Int. Cl.[7] .................................................. A01N 1/02
(52) U.S. Cl. ............................................. 435/2; 514/54
(58) Field of Search ......................... 514/54, 25; 435/2

(56) References Cited

U.S. PATENT DOCUMENTS

| | | | |
|---|---|---|---|
| 4,007,087 | 2/1977 | Ericsson | 195/1.8 |
| 4,327,177 | 4/1982 | Shrimpton | 435/2 |
| 4,605,558 | 8/1986 | Shrimpton | 424/105 |
| 5,116,969 | * 5/1992 | Adams et al. | 536/126 |
| 5,478,576 | 12/1995 | Jung et al. | 424/488 |
| 5,879,877 | * 3/1999 | Ellington et al. | 435/2 |

OTHER PUBLICATIONS

Ellington et al., "Use of a plant polysaccharide gradient to wash bull sperm improves fertilization and embryonic development", Annual Conference of the International Embryo Transfer Society, Salt Lake City, Utah, Jan. 7–10, 1996.*

Bongso, et al., "Improved Sperm Concentration, Motility, And Fertilization Rates Following Ficoll Treatment Of Sperm In A Human In Vitro Fertilization Program," *Fertility And Sterility* 51:850–854, 1989.

Brackett and Zuelke, "Analysis Of Factors Involved Production Of Bovine Embryos," *Theirogenology* 39:43–64, 1993.

Davis, "The Promise And Pitfalls Of Computer–Aided Sperm Analysis," *Infertility & Reproductive Medicine Clinics* 3:341–352, 1992.

Hill et al., "Use Of Arabinogalactan To Obtain Washed Murine Platelets Free Of Contaminating Plasma Proteins And Appropriate For Studies Of Function, Morphology, And Thrombopoiesis," *J. Lab. Clin. Med.* 111:73–83, 1988.

Jevendran et al., "Development Of An Assay To Assess The Functional Integrity Of The Human Sperm Membrane And Its Relationship To Other Semen Characteristics," *J Reprod. Fert.* 70:219–228, 1994.

Kruger et al., "New Method Of Evaluating Sperm Morphology With Predictive Value For Human In Vitro Fertilization," *Urology* 30:248–251, 1987.

Parrish et al., "Effect Of Bovine Sperm Separation By Either Swin–Up Or Percoll Method On Success Of In Vitro Fertilization And Early Embryonic Development," *Theriogenology* 44:859–869, 1995.

Prescott et al., "Larch Arabinogalactan For Hepatic Drug Delivery: Isolation And Characterization Of A 9 kDa Arabinogalactan Fragment," *Carbohydrate Research* 278:113–128, 1995.

Rogers et al., "Analysis Of Human Spermatozoal Fertilizing Ability Using Zona–Free Ova," *Fert Ster.* 32:664–670, 1979.

Stout, "Larch Arabinogalactan" in Industrial Gums, R.L. Whistle Ed., Academic Press, New York, 307–310, 1959.

Swanson et al., "Effect Of Percoll Wash On Sperm Motion Parameters And Subsequent Fertility In Intrauterine Insemination Cycles," *J. Assisted Reproduction and Genetics* 12:48–54, 1995.

Tanphaichitr et al., "Egg–Penetration Ability And Structural Properties Of Human Sperm Prepared by Percoll–Gradient Centrifugation," *Gamete Research* 20:67–81, 1988.

Trounson and Gardner, Handbook of In Vitro Fertilization, CRC Press, Boca Raton, pp. 45–50, 1994.

* cited by examiner

*Primary Examiner*—Dwayne C. Jones
(74) *Attorney, Agent, or Firm*—SEED Intellectual Property Law Group PLLC

(57) ABSTRACT

A sperm solution including arabinogalactan is provided which is useful for separating the motile sperm, to produce sperm samples which are suitable for use in a variety of diagnostic and research applications. In one embodiment, the solution includes an effective amount of arabinogalactan to permit washing or separation of the sperm, while maintaining sperm viability during the washing or separation procedure. Using the improved sperm wash, non-sperm substances that are capable of having a detrimental effect on sperm viability, such as seminal plasma, white blood cells, red blood cells, freezing extender agents, sperm debris, and media components, can be removed from the sperm sample. The inclusion of arabinogalactan in the solution has a protective effect on sperm in a sperm sample during processing. In a preferred embodiment, the arabinogalactan is ultrarefined. The improved sperm solution is compatible with sperm samples obtained from variety of different mammals, including human, bovine and equine sperm samples. The washed sperm can be used in a variety of diagnostic or research protocols including infertility testing, sperm toxicology testing and in vitro fertilization.

35 Claims, No Drawings

USE OF ARABINOGALACTAN IN A SPERM WASH PRODUCT

CROSS-REFERENCE TO RELATED APPLICATION

This application is a continuation of U.S. patent application Ser. No. 08/599,595, which was filed on Feb. 9, 1996 and which issued as U.S. Pat. No. 5,879,877.

BACKGROUND OF THE INVENTION

The present invention is generally in the area of improved solutions containing arabinogalactan for washing and separating sperm.

Sperm must be washed prior to use in most diagnostic or research protocols, such as infertility testing, in vitro fertilization and freezing. Washing is done to limit damage to the sperm cell by components of seminal plasma, such as antibodies, white blood cells, red blood cells and bacteria. Washing also removes dying or dead sperm which release enzymes and other products which are toxic to healthy sperm.

Generally, sperm are separated by allowing the motile sperm to swim away from the debris (sperm swim-up), by centrifuging the sperm through a gradient and collecting a pellet of live sperm (washing), or by passing the sperm through a column that binds the dead or unhealthy sperm. Each of these current techniques has its own disadvantages. Swim-up only recovers a small number of the normal sperm. Column methods have poor selectivity for the normal sperm in the ejaculate. Centrifugation through a density gradient results in high sperm recovery but also can produce products which are toxic to sperm, so that an additional wash step is required to remove the products. Centrifugation also can produce sperm with reduced motility and fertility during in vitro fertilization. Parrish et al., *Theriogenology*, 44:859–869 (1995); and Tanphaichitr et al., *Gamete Research*, 20:67–81 (1988).

Methods and compositions for washing and separating sperm have been the subject of many studies. Trounson and Gardner, *Handbook of In Vitro Fertilization*, CRC Press, Boca Raton, 1994, pp. 46–50. Bongso et al., *Fertility and Sterility*, 51:850–854 (1989) discloses a study of the improvement of concentration and motility of sperm following separation in Ficoll, a synthetic polymer of sucrose. U.S. Pat. No. 4,007,087 to Ericsson discloses fractionating sperm in a medium including soluble materials such as proteins, peptides and dextran. U.S. Pat. No. 4,327,177 to Shrimpton discloses the separation of sperm by density in a nutrient media derived from mammalian milk. U.S. Pat. No. 4,605,558 to Shrimpton discloses a method of separating X and Y sperm in a density gradient and an osmolality gradient in a medium derived from milk. Platov et al., *Ovtsevodstvo*, 10:38–39 (1980) (Abstract) discloses the use of gum arabic, cherry resin and apricot resin in a sheep semen freezing medium.

Arabinogalactan is a water-soluble polysaccliaride which can be isolated from trees of the genus Larix, particularly *Larix occidentalis* Nuttall (western larch). Methods for the preparation of ultrarefined arabinogalactan are disclosed in U.S. Pat. No. 5,116,969. Hill et al., *J. Lab. Clin. Med.*, 111:73–83 (1988) discloses the use of arabinogalactan to obtain washed murine platelets by centrifugation. The preparation of arabinogalactan derivatives and fragments is described in Prescott, et al., *Carbohydrate Research*, 278:113–128 (1995); and U.S. Pat. No. 5,478,576 to Jung, et al., the disclosures of which are incorporated herein by reference.

There is a need for the development of improved products for washing and separating sperm for protocols such as infertility testing, in vitro fertilization, and freezing.

It is therefore an object of the invention to provide solutions for washing and separating sperm to produce sperm samples with optimal motility and viability, and which can be used in a variety of diagnostic and research applications, such as fertility testing, and in vitro fertilization.

SUMMARY OF THE INVENTION

Compositions including arabinogalactan, and methods for their use in washing and separating sperm are provided. Use of solutions including arabinogalactan produces motile sperm samples which are suitable for use in a variety of diagnostic and research applications. In one embodiment, the wash is provided with an effective amount of arabinogalactan to permit washing or separation of the sperm, while maintaining sperm viability properties during the washing or separation procedure. Using tie improved sperm wash solution, non-sperm substances that are capable of having a detrimental effect on sperm viability, such as seminal plasma, white blood cells, red blood cells, freezing extender agents, sperm debris, and media components, are removed from the sperm sample. The inclusion of arabinogalactan in the wash allows the motile sperm to be separated without damage to these sperm. In a preferred embodiment, the arabinogalactan is ultrarefined.

The improved sperm wash product is compatible with sperm samples obtained from variety of different mammals, including human, bovine and equine sperm samples. The sperm wash including arabinogalactan can be used to separate motile sperm, while optimizing a wide range of viability properties of the sperm, including sperm motility, sperm numbers, percentage of living sperm recovered, sperm membrane function, sperm penetration rate, sperm fertilization rate and/or oocyte development following fertilization. The washed sperm may be used in a variety of diagnostic or research protocols including infertility testing, sperm toxicology testing, and in vitro fertilization.

DETAILED DESCRIPTION OF THE INVENTION

A sperm wash solution including arabinogalactan, which is highly compatible with sperm is provided, as well as methods for using the wash to wash or separate sperm, to produce sperm which can be used in a variety of diagnostic or research applications. The presence of arabinogalactan in the solution has a protective effect on sperm in a sample during processing. In a preferred embodiment, the arabinogalactan is ultrarefined. The concentration of arabinogalactan in the solution can be optimized for a particular sperm to sample. Sperm washed in a solution comprising arabinogalactan have improved properties in comparison to sperm processed in existing sperm wash products, including improved sperm motility, sperm numbers, percenage of living sperm, sperm membrane function, sperm penetration rate, sperm fertilization rate and oocyte development following fertilization.

Arabinogalactan

Arabinogalactan ("AG") is a water-soluble polysaccharide which can be isolated from trees of the genus Larix, particularly *Larix occidetitalis* Nuttall (western larch). Arabinogalactan may constitute up to 35% of the total heartwood of some species. Stout, "Larch Arabinogalactan" in *Industrial Gums*, R. L. Whistle Ed., Academic Press, New York, pp. 307–310, 1959. It is highly water soluble and can be purified from larch chips.

As used herein, the term "arabinogalactan," unless otherwise specified, includes naturally occurring or synthetic arabinogalactan, portions of arabinogalactan, such as degradation products, and chemically or 25 biochemically modified arabinogalactan or portions thereof which have been modified using methods available in the art, which are effective in a sperm solution during sperm washing or separation to protect sperm motility.

In one preferred embodiment, ultrarefined arabinogalactan is used in the sperm wash. Methods for the preparation of ultrarefined arabinogalactan are disclosed in U.S. Pat. No. 5,116,969, the disclosure of which is incorporated herein by reference. Ultrarefined arabinogalactan of greater than 95%, or optionally, greater than 99.9% purity (Larex UF™) is available from Larex, International, St. Paul, Minn. As defined herein "ultrarefined arabinogalactan" refers to arabinogalactan, isolated from a plant source such as trees of the genus Larix, with a purity greater than 95%. In a preferred embodiment, the molecular weight of the ultrarefined arabinogalactan is between about 10,000 and 30,000 daltons (by size exclusion chromatography with pullulan reference).

Arabinogalactan provides a useful low cost alternative to the use of other compositions commonly used in sperm washing products, such as Percoll™, colloidal polyvinylpyrrolidone coated silica, available, for example, from Sigma Chemical Company, St. Louis, Mo. The use of Percoll gradients in centrifugation for washing sperm is described, for example, in Parrish et al., *Theriogenology*, 44:859–869 (1995); Tanphaichitr et al., *Gamete Research*, 20:67–81 (1988); Trounson and Gardner, *Handbook of In Vitro Feltilization*, CRC Press, Boca Raton, 1994, pp. 46–50; and Swanson et al., *J. Assisted Reproduction and Genetics*, 12:48–54 (1995).

Arabinogalactan from Laor trees is useful since it is extremely water-soluble, occurs naturally with a very narrow molecular weight distribution, and is highly branched and thus not subject to viscosity problems. A sperm wash including arabinogalactan is easy to use, and no complicated procedures are required to produce the washed or separated sperm sample. In conventional sperm washing procedures, after centrifugation in a Percoll™ gradient, components which are toxic to sperm in the sperm sample must be washed prior to further use. This complicates the procedure and further damages sperm membranes. In contrast, there is no such requirement for a second wash for sperm washed in a product including arabinogalactan.

The presence of arabinogalactan in a sperm wash has substantially no apparent negative effect on sperm, and has, in fact, a protective effect on sperm function. In contrast to prior art compositions, the use of arabinogalactan in a sperm wash protects sperm motility, subsequent sperm lifetime in vitro, and is non-toxic.

Sperm Solutions

In one embodiment, the sperm solution is formed by adding ultrarefined arabinogalactan powder, such as Larex UF™, available from Larex, International, St. Paul, Minn., to a balanced salt solution. Such solutions generally include selected salts, sugar and water, and other compositions selected for the particular animal from which the sperm sample is derived. Methods for the preparation of standard sperm solutions to which AG can be added, are described, for example, in Trounson and Gardner, *Handbook of In Vitro Fertilization*, CRC Press, Boca Raton, 1994. Arabinogalactan also can be added to solutions such as human tubal fluid, or to Tyrode's lactate, albumin and pyruvate ("TALP"), which is described in Table 1.

The concentration of ultrarefined arabinogalactan in the wash solution is generally between about 15–50% weight/volume ("w/v"). The concentration of arabinogalactan in the solution can be modified and optimized for a particular sperm sample. In one embodiment, the concentration of arabinogalactan is between about 20 and 40% w/v, for example, about 20 to 30% w/v in the aqueous solution. In a preferred embodiment, a concentration of about 25 to 30% w/v is used in the solution for mammalian sperm. For example, for domestic animal sperm samples, such as bovine and equine sperm samples, a concentration of about 22% w/v AG in TALP is used in a preferred embodiment, while for human sperm, a concentration of about 30% w/v AG in human tubal fluid is preferred.

As used herein, arabinogalactan "solutions" includes both solutions and suspensions of arabinogalactan. For sperm separation or wash processing, the sperm medium containing arabinogalactan and the sperm sample is maintained generally at a temperature ranging from about 20 and 30° C. The solution optionally can be cooled or frozen for storage of the sperm sample, for example, after sperm washing. The pH can be selected for a particular sperm sample or application, and generally is in the range of about 7.4 to 7.8, preferably about pH 7.4.

Sperm Processing

The arabinogalactan-containing sperm solution can be used to process sperm in a sperm sample in a variety of protocols including washing sperm to remove non-sperm substances or separating sperm on the basis of sperm motility, for example by centrifugation or by column filtration.

In one embodiment, a wash solution for sperm is provided, which includes an effective amount of arabinogalactan to remove non-sperm substances, or non-motile sperm or sperm fragments, from the sample, while also maintaining sperm viability properties during washing. Sperm is washed prior to use in diagnostic or research protocols, to limit damage to the sperm cell by other substances in the sperm sample. Components which can be removed from a sperm sample by washing in a solution comprising arabinogalactan include seminal plasma, proteins, antibodies, white blood cells, red blood cells, freezing extender agents, such as egg yolk, sperm debris, such as non-motile, or non-living sperm or sperm fragments, as well as culture media and media supplements. In another embodiment, motile sperm can be separated from other less motile sperm in a sperm sample, in a solution provided with an effective amount of arabinogalactan to maintain and/or protect the viability properties, such as sperm motility, of the sperm in the sample during the separation process. Washing or separating sperm in a sperm solution including arabinogalactan produces sperm samples with improved viability properties in comparison to sperm obtained using standard sperm wash formulations available in the art.

In an exemplary procedure, sperm in a sample are washed or separated on the basis of motility by centrifugation in a solution comprising ultrarefined arabinogalactan. The AG containing wash is filtered with a 0.2 micron filter and is placed into sterile centrifuge tubes. Samples of sperm are placed over a 4–5 ml continuous column of the AG solution and centrifuged (washed). The ratio of sperm sample to wash solution is, for example, about 1:2. The sperm then is forcibly washed through the AG gradient by centrifugation at 300×g for about 20–30 min. After washing, the wash product is removed and discarded, and the pellet of sperm cells at the bottom of the tube is ready for use in diagnostic or research protocols. Sperm washed or separated through the AG gradient significantly swim faster, have less membrane damage, and are able to fertilize more oocytes than sperm washed through standard solutions such as Percoll™ systems. The washed sperm sample also may be frozen and stored in the arabinogalactan-containing medium.

Sperm Testing

A sperm solution is provided for processing a sperm sample to isolate the motile sperm with an effective amount of arabinogalactan to wash and maintain the viability properties of the sperm sample following processing in procedures such as sperm washing or separation. The use of arabinogalactan in the solution protects sperm viability during processing, in comparison to standard sperm wash. Sperm viability properties which can be protected, in comparison to results obtained using standard sperm wash, include sperm motility, sperm numbers, percentage of living sperm recovered, sperm membrane function, sperm penetration rate, sperm let vitro fertilization rate and/or oocyte development following fertilization.

Sperm samples processed in a wash including arabinogalactan may be tested for different sperm viability properties, or used in diagnostic or research applications using methods available in the art. Sperm numbers in a suspension can be determined by manual or computerized methods. Using computerized methods, a sperm suspension is applied to a counting chamber available in the art such as a Makler™ (Fertility Technology, Natick, Mass.) counting chamber, and the number of sperm is counted, which is equal the number of sperm/ml in the original suspension.

Sperm morphology or shape is determined, for example, by smearing 10 μl of a sperm sample onto a slide and staining with a differential stain such as Wright Giemsa at 0.1% (w/v) for 30 min. Sperm then are observed under a microscope and categorized as to normal or abnormal shapes (morphology), as described in Kruger et al., *Urology*, 30:248 (1987).

Motility of sperm is expressed as the total percent of motile sperm, or the speed of the sperm that are motile and can be determined using methods available in the art, such as by subjective visual determination using a phase contrast microscope, or using a computer automated semen analyzer. Using phase contrast microscopy, the sample is analyzed visually to group sperm into total percent motile (swimming), and total percent progressively motile (swimming forward), or the speed of the sperm which are progressively motile, i.e., fast, medium, or slow. Using a computer, the track speed of individual sperm is analyzed. Data is expressed as the percent motile, as well as the mean path velocity and track speed of sperm in the sample.

Sperm viability as a measurement of the percentage of living sperm is determined by membrane exclusion stains available in the art. Sperm membrane function of live sperm is tested by placing sperm into a low salt (hypo-osmotic) solution. This causes sperm with healthy membranes to pump salt out of the cell, and causes the membranes of the sperm to shrink as the cell grows smaller. The sperm tail then curls inside this tighter membrane. Sperm with a curled tail are the sperm which are healthy and have functional membranes. The number of sperm with a curled tail then is expressed as a percent of the total number of sperm present.

To assay sperm penetration, the ability of capacitated sperm to penetrate a dead zona free hamster egg is measured. Sperm in vitro fertilization rates are determined by measuring the percent of oocytes fertilized in vitro using methods available in the art. The capacitated sperm sample is incubated with oocytes, and at the end of the incubation, the percentage of oocytes fertilized is determined, or the fertilized oocytes are left in culture, division occurs and the number of cleaving embryos is determined.

Sperm Cell Type

An arabinogalactan-containing solution is compatible with sperm cells from a variety of different animals. The solution can be formulated with a concentration of arabinogalactan and other components in the solution suitable for the type of sperm cells being processed. For example, the solution may be formulated for use with bovine, equine, porcine, human, murine, rodent, canine, avian, or rabbit sperm samples. The solution can be used to wash sperm samples from a variety of different mammals, and then the sample can be used directly in wide range of diagnostic or research protocols such as sperm toxicology and fertility testing.

Processing sperm samples from a variety of different animals in the solution including arabinogalactan results in significantly improved protection of sperm function, such as a higher recovery of motile sperm, improved motility of the sperm, longer lifetime of the sperm in subsequent culture, increased oocytes fertilization, and improved ability of zygotes to form normal blastocysts, in comparison to prior art methods.

Applications

An arabinogalactan-containing sperm solution can be used in a variety of applications. Sperm can be washed in arabinogalactan-containing solutions to permit the selection and separation of the most motile sperm in the sample for use in different diagnostic and research protocols. Sperm samples can be processed by, for example, separation or washing in a solution including arabinogalactan, and then can be used in a variety of diagnostic or research protocols including infertility testing, and sperm toxicology testing. Examples of infertility tests include tests of sperm motility, percent living sperm, sperm count, membrane function, penetration rate and in vitro fertilization rate. Protocols available in the art may be used which are suitable for a particular sperm cell type and a particular diagnostic or research application.

In one embodiment, sperm solutions including arabinogalactan at a preselected concentration for a particular sperm sample are provided in prefilled tubes. The product also can be provided in solution in a dispenser for a particular application. In one embodiment, centrifuge tubes for use with bovine and equine sperm are provided which include a sterilized 22% w/v solution of ultrarefined arabinogalactan in TALP. The tubes may be kept under refrigeration until use. During use, sperm samples are layered on top of the arabinogalactan gradient and the tube is centrifuged for 25 min at 300×g.

Thus, the arabinogalactan-containing wash is useful for washing and separating sperm. The arabinogalactan-containing solution can be used to process sperm samples to produce motile sperm samples for use in a variety of different diagnostic and research applications.

The present invention will be further understood by reference to the following non-limiting examples.

Methods and Materials

In the following examples, sperm cells from the male are obtained either from a fresh ejaculate in raw semen or a stored sample processed by washing or extending and refrigerated or frozen. All supplies and equipment were obtained from Gibco or Fertility Technologies, Natick, Mass.

Sperm testing assays available in the art were used in Example 1. Numbers of sperm present in a suspension of sperm medium were determined manually. For example, 6 μl of sperm suspension is applied to a Makler™ counting chamber and the number of sperm counted in 10 squares is determined, which is equal the number of sperm/mi in the original suspension.

Sperm motility was determined using computerized methods using a Hamilton Thorn, Beverly, Mass. semen analyzer, wherein the track speed of individual sperm is analyzed (Davis, *Infertility & Reproductive Medicine Clinics* 3:341, 1992). A 7 μl sperm sample is placed onto a slide or chamber designed for computer automated semen analysis ("CASA") and the computer tracks individual sperm cells and determines their motility as to speed over distance. Data is then expressed as a percent motile and specific measurements are given for parameters such as mean path velocity, and track speed.

The percent of live sperm in a sample was determined using membrane exclusion stains. Samples of sperm are incubated with viable dyes such as Hoechst 33258 (Sigma Chemical Co., St. Louis, Mo.) or eosin-nigrosin. Dead sperm have disrupted membranes which allow the stain to access the interior of the cell causing a staining pattern. For example, a 10 μl aliquot of eosin-nigrosin stain (Society for Theriogenelogy, Hastings, Nebr.) is mixed with 10 μl of a sperm sample. The mixture then is smeared across a slide, and the number of dead (pink) and white (live) sperm are counted. The number of unstained cells (live) divided by the total number of sperm gives the percentage of live sperm present.

Functional membrane health of a sperm cell was determined by the hypo-osmotic swell test ("HOS"). In this test, a hypo-osmotic solution including 75 mmol/L fructose and 25 mmol/L sodium citrate is prepared. One ml of this solution is added to 100 μl of sperm sample. After incubation for 30 min, a 10 μl aliquot of this mixture is placed on a slide, and the percentage of sperm with curled tails counted (Jeyendran et al., *J Reprod. Fert.* 70:219, 1984).

Sperm penetration tests were conducted as described in Rogers et al., *Fert Ster.*, 32:664, 1979). A dead zona free hamster egg (commercially available, Fertility Technologies, Natick, Mass.), is used for all species. Sperm are capacitated by incubation with 10 IU heparin. The capacitated sperm (100,000 in 100 μl BWW medium, Fertility Technologies) then are incubated with hamster oocytes for 3 hours, the oocytes are stained with 1% acetolacmoid, and the number of sperm penetrating each one is counted.

In vitro fertilization rates were determined by maturing oocytes in vitro using M199 (Gibco) with 50 μg luteinizing hormone for 22 hours, as described in Brackett and Zuelke, *Therio.*, 39:43, 1993. Sperm are chemically capacitated either by incubating with 10 IU of lieparin (bull sperm) or by an 18 hour incubation with bovine serum albumin ("BSA") (human sperm), and then incubated with oocytes for 24 hours. Oocytes then are stained with a 1% aceto-orcein stain to determine the percent fertilized, or left in culture to divide and form embryos.

EXAMPLE 1

Sperm Tests

Bovine, human and equine sperm samples were washed by centrifugation in a sperm wash including either arabinogalactan, or Percoll™, the industry standard, then were tested for sperm viability properties including sperm motility, percent living sperm, count, membrane function, penetration and fertilization.

Sperm Wash

A continuous gradient of a sperm washing solution was prepared including a balanced salt solution together with ultrarefined arabinogalactan. The sperm wash were prepared for the sperm from different animals as follows: glucose-free Tyrode's lactate, albumin, and pyruvate containing medium ("TALP", see Table 1) for bovine sperm, glucose-containing TALP (5 mM glucose) for other animal species' sperm, and HTF (human tubal fluid obtained from Irvine Scientific, La Jolla, Calif., or Fertility Technologies, Natick, Mass.) for human sperm. The TALP was made up in water with the concentrations shown in Table 1.

TABLE 1

| Glucose Free TALP Medium | |
|---|---|
| Ingredient | per 500 ml |
| NaCl | 2.922 g |
| KCl | 0.1156 g |
| $NaHCO_3$ | 1.0500 g |
| $NaH_2PO_4H_2O$ | 0.0200 g |
| Na Lactate syrup (60%) | 1841 μl |
| $CaCl_2$ | 0.1546 g |
| MgCl | 0.0407 g |
| Phenol Red | 0.0050 g |
| Hepes | 1.1915 g |
| BSA Fraction V | 3.000 g |
| Genatmycin Sulfate | 500 μl |
| Na Pyruvate | 25 ml |

Ultrarefined arabinogalactan (UF, available from Larex International, Inc., St. Paul, Minn.) was added to the solution ("the AG wash"). The concentration of arabinogalactan ("AG") was about 22% w/v for animal sperm and about 30% for human sperm samples. In the control, a double density of 45% w/v over 90% w/v Percoll™ was used ("the Percoll wash"). The mixture was filtered through a 0.2 micron filter into a centrifuge tube prior to use. The pH of the arabinogalactan-containing wash was adjusted to about pH 7.4 before sperm sample addition.

Sperm Centrifugation

A semen sample was placed over the wash product at a ratio of 1 part semen to 2 parts wash. The total volume of the semen sample and the wash was typically about 9 ml for humans and 4 ml for bovine. The sample then was centrifuged at 300×g for 20–30 min. The AG wash or Percoll wash was then aspirated off. The pellet of sperm obtained after washing was then resuspended in a balanced salt solution and assayed as described above. The sperm wash including arabinogalactan was stable and remained effective for the sperm wash even after storage for 2 months, thus indicating the long term stability of the solution.

In the sperm washing centrifugation procedure using Percoll™, (the Percoll™ procedure), after centrifugation it is necessary, and customary in the art, to wash the sperm pellet again in a solution with no Percoll™, to remove the Percoll™, which is toxic to sperm. Advantageously, there was no such requirement in the sperm washing procedure using AG ("the AG procedure"), and, in fact, improved results were obtained without a second wash. In the following experiments, therefore, a second wash (centrifugation) was conducted after the Percoll™ procedure, but not in the AG procedure.

Bovine Sperm Assay

Frozen sperm from 4 bulls was washed by centrifugation in the AG or Percoll™ products as described above. Each experiment was duplicated at least twice. Data are expressed as mean±SEM.

The AG procedure produced a higher % recovery of sperm using manual counting (p=0.1) than did the Percoll™ procedure (61±9% vs. 53±5%). The AG procedure also recovered a higher % (p=0.08) of motile (swimming) sperm from the original sample using the computerized motility assay than did the Percoll™ procedure (88±9% versus 73±6%).

Sperm recovered from the AG wash did not differ greatly (p=0.18) in their percent motility using the computerized motility assay versus that in Percoll™ (95±0.25% versus 90±3%). However, the variability of sperm motility after wash through the AG procedure was very low (0.25%), suggesting that the AG wash more consistently supported high sperm motility.

The survival of sperm in routine culture conditions after washing also was assayed. After incubation for 30 minutes, motility was greater (p=0.08) for sperm originally washed in AG wash than in Percoll™ (94±2% versus 88±9%). After 4 hr, motility did not significantly differ (p=0.5) for sperm from either treatment (74±14% versus 70±18%). After 8 hr, there was no substantial difference. After 24 hr, there were visually more sperm motile and alive under an inverted microscope for those separated by the AG wash (p=0.03) than the Percoll™ wash. In fact, few, if any, sperm were still alive from the Percoll™ wash group, whereas sperm from the AG wash consistently lived to at least 36 hr in culture.

The sperm velocity characteristics also were determined. Sperm swam faster after washing in the AG wash (p±0.05) versus the Percoll™ wash. After washing, the following characteristics were observed using the AG procedure vs. the Percoll™ procedure: the path velocity was 84±4 versus 71±3 un/sec; the mean track speed was 118±4 versus 97±5 un/sec; and the progressive velocity was 71±4 versus 60±5 un/sec.

In vitro fertilization data also were obtained. In vitro matured bovine oocytes were fertilized with frozen bull sperm during 3 runs. A total of 1094 oocytes were involved in the study, 550 were used with AG washed sperm and 545 with Percoll™ washed sperm. Cleavage rates for the oocytes was significantly superior after washing sperm through AG wash versus through Percoll™ (p=0.001) as illustrated below in Table 2.

TABLE 2

Oocyte Cleavage Rates

|  | Mean % fertile ± SEM | Range |
| --- | --- | --- |
| AG wash | 73 ± 2% | 62–84% |
| Percoll ™ | 53 ± 3% | 44–59% |

The percentage of fertile oocytes able to develop normally in culture to form blastocysts after one week was significantly superior after washing sperm through AG wash versus through Percoll™ (p=0.009) as shown below in Table 3.

TABLE 3

Oocyte Development

|  | Mean % blastocysts ± SEM | Range |
| --- | --- | --- |
| AG wash | 59 ± 4% | 53–66% |
| Percoll ™ | 26 ± 5% | 20–41% |

The overall production of blastocysts (normally developed embryos), as a percentage of total oocytes introduced into the system was significantly superior after washing sperm through AG wash versus through Percoll™ (p=0.004) as illustrated in Table 4.

TABLE 4

Blastocyte Production

|  | Mean % oocytes to blastocysts | Range |
| --- | --- | --- |
| AG wash | 43 ± 4% | 38–51% |
| Percoll ™ | 18 ± 3% | 14–24% |

(a) Total cell counts for blastocysts formed after fertilization with either AG wash or Percoll™ treated sperm did not differ (p=0.25).

TABLE 5

Cell Counts

|  | Total cell number ± SEM | Range |
| --- | --- | --- |
| AG wash | 85 ± 2 | 34–112 |
| Percoll ™ | 88 ± 2 | 46–110 |

This suggests that even though more oocytes developed into blastocysts after sperm treatment with AG wash, the basic mechanisms of embryonic development are not changed.

Thus, frozen bull sperm washed through AG wash without a follow up wash had significantly superior properties in comparison to sperm washed through a standard Percoll™ system in that more sperm were recovered; sperm swim faster; sperm live longer in culture; more sperm are able to fertilize an egg; and more fertilized eggs continue to develop.

Equine Sperm Assay

Sperm from 4 stallions was extended and cooled overnight, and washed through AG wash or Percoll™ medium by centrifugation as described above. Stallion sperm is not usually processed with Percoll™ because it prematurely capacitates the sperm. The percent of motile sperm was greater after treatment in AG wash than in the Percoll™ wash (p=0.04, 60±8% versus 30±10%). The % of sperm with normal membrane function using the hypo-osmotic swell test was higher after washing in AG (p=0.02) than in Percoll™ (70±5% versus 32±12%). Two stallions with poor initial quality of sperm were observed to have almost a doubling in the percent motile sperm and the percent normal membranes after washing through the AG solution.

Human Sperm Assay

Freshly ejaculated semen from 12 men was used. The optimal concentration of AG for the sperm wash (centrifugation) was found to be about 30% w/v in a 4 ml gradient. The donors had both normal and abnormal semen quality, and the mean initial motility was 48±12%. The percent of motile sperm obtained using the AG wash or the Percoll™ wash did not differ greatly. Sperm penetration rate tested using the zona free hamster egg assay showed that there was no substantial difference in tile percent of eggs penetrated or of numbers of sperm able to penetrate using the AG or Percoll™ procedures, although one donor's sample had a 30% improvement in sperm penetration after washing using the AG wash versus the Percoll™ wash. The percent of sperm with normal membrane function using the hypo-osmotic swell test was higher (p=0.06) after washing with the AG wash than using Percoll™ (70±13% versus 46±10%). Thus, in human sperm samples, membrane damage is reduced.

Conclusion

Sperm which were washed by centrifugation as described above in a wash solutions including arabinogalactan had improved properties in comparison to sperm washed in a solution including a Percoll™ gradient. More motile sperm were recovered, recovered sperm had better motility (swim faster), had less membrane function damage, and had higher fertilization rates in in vitro fertilization.

Modifications and variations of the present invention will be obvious to those skilled in the art from the foregoing detailed description. Such modifications and variations are intended to come within the scope of the following claims.

What is claimed is:

1. A method for washing a sperm sample comprising washing the sperm sample in a sperm solution comprising an effective amount of arabinogalactan to permit removal of non-sperm substances from the sample and to protect one or more sperm viability properties during washing.

2. The method of claim 1 wherein the non-sperm cell substances are selected from the group consisting of seminal plasma, white blood cells, red blood cells, freezing extender agents, sperm debris, culture media and media supplements.

3. The method of claim 1 wherein the sperm viability property is selected from the group consisting of sperm motility, sperm numbers, percentage of living sperm, sperm membrane function, sperm penetration rate, sperm fertilization rate and oocyte development following fertilization.

4. The method of claim 1 wherein the arabinogalactan is ultrarefined.

5. The method of claim 4 wherein the concentration of arabinogalactan in the solution is between about 20% and 30% weight/volume.

6. The method of claim 4 wherein the sperm sample is purified by centrifugation of the sperm sample in the solution comprising arabinogalactan.

7. The method of claim 4 wherein the arabinogalactan is selected from the group consisting of naturally occurring or synthetic arabinogalactan, portions of arabinogalactan, and chemically or biochemically modified arabinogalactan or portions thereof.

8. The method of claim 4 further comprising using the washed sperm in a protocol selected from the group consisting of diagnostic or research testing.

9. The method of claim 4 further comprising using the washed sperm in a sperm testing protocol selected from the group consisting of a sperm motility test, a test of percent living sperm, sperm counting, a sperm membrane function test, a sperm penetration rate test and a sperm in vitro fertilization rate test.

10. The method of claim 1 further comprising providing in the solution a concentration of arabinogalactan which is suitable for the sperm sample being washed.

11. The method of claim 10 wherein the sperm sample is selected from the group consisting of bovine, equine, porcine, human, murine, rodent, canine, avian, and rabbit sperm samples.

12. A method for separating motile sperm from other sperm in a sperm sample, the method comprising separating sperm in the sample in a solution comprising arabinogalactan, wherein the arabinogalactan protects one or more sperm viability properties during separation.

13. The method of claim 12 wherein the separated sperm have improved ability to fertilize an oocyte in comparison to the other sperm, after separation.

14. The method of claim 12 wherein the arabinogalactan is ultrarefined.

15. The method of claim 14 wherein the concentration of arabinogalactan in the solution is between about 20% and 30% weight/volume.

16. The method of claim 14 further comprising using the separated sperm in a protocol selected from the group consisting of diagnostic or research testing.

17. The method of claim 12 wherein the sperm are separated based on motility using a method selected from the group consisting of centrifugation and column filtration in the solution comprising arabinogalactan.

18. The method of claim 12 further comprising providing in the solution a concentration of arabinogalactan which is suitable for the type of sperm being separated.

19. The method of claim 18 wherein the sperm sample is selected from the group consisting of bovine, equine, porcine, human, murine, rodent, canine, avian, and rabbit sperm samples.

20. The method of claim 12 wherein the solution comprises an effective amount of arabinogalactan to protect one or more sperm viability properties of sperm in the sample during separation.

21. The method of claim 12 wherein the arabinogalactan is selected from the group consisting of naturally occurring or synthetic arabinogalactan, and derivatives and fragments of arabinogalactan.

22. An improved composition for washing or separating sperm in a sperm sample, comprising a sperm solution provided with an effective amount of arabinogalactan to permit protection of one or more sperm viability properties during sperm washing or separation.

23. The composition of claim 22 wherein the arabinogalactan is ultrarefined.

24. The composition of claim 23 wherein the concentration of arabinogalactan in the solution is between about 15–50% weight/volume.

25. The composition of claim 23 wherein the concentration of arabinogalactan in the solution is between about 20% and 30% weight/volume.

26. The composition of claim 22 further comprising a sperm sample.

27. The composition of claim 26 wherein the sperm sample is selected from the group consisting of bovine, equine, porcine, human, murine, rodent canine, avian, and rabbit sperm samples.

28. The composition of claim 22 for processing a bovine or equine sperm sample, wherein the solution further comprises lactate, albumin and pyruvate.

29. The composition of claim 28 wherein the pH of the solution is about 7.4.

30. The composition of claim 22 for processing a human sperm sample, wherein the solution further comprises human tubal fluid.

31. The composition of claim 30 wherein the pH of the solution is about 7.4.

32. The composition of claim 22 further comprising providing in the solution a concentration of arabinogalactan which is suitable for the sperm sample being washed or separated.

33. The composition of claim 32 wherein the concentration of arabinogalactan in the solution is suitable for a sperm sample selected from the group consisting of bovine, equine, porcine, human, murine, rodent, canine, avian, and rabbit sperm samples.

34. The composition of claim 22 wherein the arabinogalactan is selected from the group consisting of naturally occurring or synthetic arabinogalactan, and derivatives and fragments of arabinogalactan.

35. An improved composition for washing or separating sperm in a sperm sample, comprising a sperm solution provided with an effective amount of arabinogalactan to improve during washing or separation a sperm function selected from the group consisting of sperm motility, percentage of living sperm, sperm membrane function, sperm penetration rate, sperm fertilization and oocyte development following fertilization.

* * * * *